United States Patent [19]
Franke et al.

[11] Patent Number: 5,443,948
[45] Date of Patent: Aug. 22, 1995

[54] PROCESS FOR PREPARATION OF A PHOTOGRAPHIC ELEMENT

[75] Inventors: Mark D. Franke, Greenville, S.C.; Richard J. Legg, Colts Neck, N.J.; Alden D. West, Hendersonville, N.C.; Anna E. Doyle, Westfield, N.J.

[73] Assignee: E. I. Du Pont de Nemours and Company, Wilmington, Del.

[21] Appl. No.: 215,389

[22] Filed: Mar. 21, 1994

Related U.S. Application Data

[63] Continuation of Ser. No. 995,514, Dec. 21, 1992, abandoned.

[51] Int. Cl.$^6$ .................. G03C 1/14; G03C 1/22; G03C 1/28
[52] U.S. Cl. ................ 430/572; 430/576; 430/583; 430/588; 430/592; 430/607; 430/609; 430/614; 430/630
[58] Field of Search .......... 430/569, 570, 572, 576, 430/577, 581, 583, 588, 591, 592, 593, 607, 609, 614, 630

[56] References Cited

U.S. PATENT DOCUMENTS

| | | | |
|---|---|---|---|
| 3,208,977 | 9/1964 | Schoenthaler et al. | 430/548 |
| 3,529,963 | 9/1970 | Marchese | 430/353 |
| 3,647,464 | 3/1972 | Smith et al. | 430/465 |
| 3,933,507 | 1/1976 | van Konig et al. | 430/570 |
| 4,336,328 | 6/1982 | Brown et al. | 430/569 |
| 5,112,731 | 5/1992 | Miyasaka | 430/567 |

*Primary Examiner*—Janet C. Baxter

[57] ABSTRACT

An improved process for manufacturing a spectrally sensitized photographic element comprising the combination of ultrafiltration of silver halide grains in combination with a supersensitizing additive consisting of

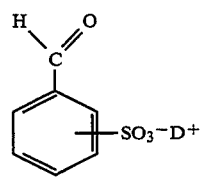

Formula 1 or

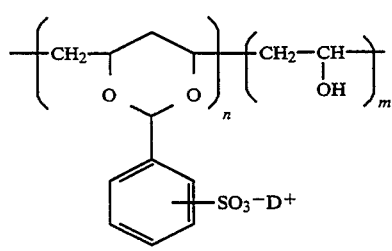

Formula 2 wherein $D^+$ is $Na^+$, $K^+$, $Li^+$, $NH_4^+$; n is 1–5; m is 1–10.

17 Claims, No Drawings

PROCESS FOR PREPARATION OF A PHOTOGRAPHIC ELEMENT

This is a continuation of application Ser. No. 07/995,514 filed Dec. 21, 1992, now abandoned.

FIELD OF INVENTION

This invention is related to improvements in the preparation of a photographic element. More specifically this invention is related to a process for preparing a photographic element with improved sensitometric properties.

BACKGROUND OF THE INVENTION

Photographic elements are widely known to utilize a silver halide grain as an image capture material. The preparation of silver halide grains is also widely known in the art to involve the reaction product of a soluble silver salt with a soluble halide salt in the presence of a peptizer such as gelatin or the like. Subsequent to formation of the silver halide crystals it is desirable to increase the sensitivity of the crystals with spectral sensitizing dyes as known in the art.

During the formation of the desired insoluble silver halide salt a host of deleterious reaction products are typically formed. These deleterious reaction products are predominantly soluble salts which are known to impede the spectral and chemical sensitization and it is therefore desirable to remove these deleterious reaction products.

Methods of removing the deleterious reaction products include a variety of methods which can be categorized as either precipitation or ultrafiltration. Precipitation involves coagulation of the peptizer to form a solid phase, which contains the silver halide grains, and a liquid phase which contains the deleterious reaction products. Removing the liquid phase separates the grains from the deleterious products. Virgin liquid can be added and the peptizer uncoagulated to obtain the desired product. If desired, the coagulation step can be repeated to reach optimal purity. Precipitation methods are undesirable due to the limited control and the poor reproducibility of the impurity levels in the finished product. Furthermore, the addition of a coagulating agent may increase the viscosity of the resulting solution which is undesirable in the subsequent coating of the silver halide grains on a substrate.

Ultrafiltration is an improvement over precipitation. Undesirable soluble reaction products are removed by passing the solution through a filtering means which is chosen to exclude passage of desirable silver halide grains but not soluble reaction products. The exit stream, or flitrate, and retentate can be monitored and the process stopped at a predetermined level of purity which allows for the formation of a product which is more reproducible than those obtained by the precipitation methods.

Ultrafiltration is thought to affect the surface of silver halide grains in a way which is deleterious to the aggregation of some classes of sensitizing dyes. There has been a long felt need in the art to provide a means for supersensitizing ultrafiltered grains such that the advantages of ultrafiltration and the advantages of spectral sensitizing dyes can be realized in combination.

SUMMARY OF THE INVENTION

It is an object of the present invention to provide for an improved sensitization procedure. A particular advantage of the improved sensitization procedure is the ability to realize the improved properties of grains purified by ultrafiltration in combination with spectral sensitization. These and other advantages, as will be realized by one skilled in the art, are provided in the improved process for the preparation of a photosensitive silver halide emulsion which comprises the steps of:

a) reacting $Ag^+NO_3^-$ with $G^+X^-$ to form $Ag^+X^-$ and $G^+NO_3^-$; $G^+$ is $Na^+$, $K^+$, $NH_4^+$ or a combination thereof; $X^-$ is $Cl^-$, $Br^-$, $I^-$ or a combination thereof;

b) decreasing the concentration of $G^+NO_3^-$ by ultrafiltration;

c) adding at least one of

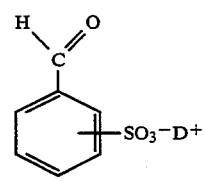

Formula 1 or

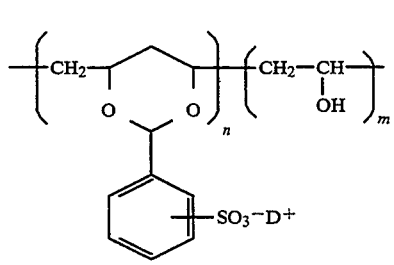

Formula 2 wherein $D^+$ is $Na^+$, $K^+$, $Li^+$, $NH4+$; n is 1-5; m is 1-10;

d) adding at least one spectral sensitizer capable of increasing the sensitivity to actinic radiation.

The teachings of the present invention provide for improved sensitometry as evidenced by the two classes of dyes represented by Formula 3 and Formula 4. Formula 3 is a spectral sensitizer defined as

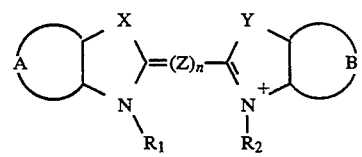

Formula 3

X,Y is oxygen or sulfur;

n is an integer chosen from the set consisting of 1, 3, 5 and 7;

A, B is a substituted aromatic ring or an unsubstituted aromatic ring;

Z represents a methine, oxazole or thiazole provided that no more than one Z is oxazole or thiazole, $R_1$ is an alkyl group or a substituted alkyl group;

$R_2$ is an alkyl group or a substituted alkyl group; and

Formula 4 is a spectral sensitizer defined as

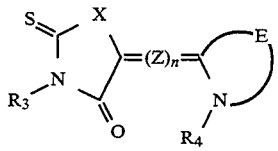

Formula 4

- X is oxygen or sulfur;
- n is an integer chosen from the set consisting of 0, 2, 4 and 6;
- E is a substituted aromatic ring or an unsubstituted aromatic ring;
- Z represents a methine, oxazole and thiazole provided that no more than one Z is oxazole or thiazole;
- $R_3$ is an alkyl group or a substituted alkyl group;
- $R_4$ is an alkyl group or a substituted alkyl group.

DETAILED DESCRIPTION OF THE INVENTION

It is known in the art to prepare a photosensitive silver halide element followed by sensitization. Intermediate to these two steps it is necessary to remove impurities. One technique for removing impurities is ultrafiltration. Another technique is the use of a coagulant. Both of these results are known to provide a satisfactory product.

The present invention provides an improvement over the prior art by the use of ultrafiltration combined with a coagulating agent which acts as a supersensitizer under the conditions as taught herein.

Supersensitizers of Formula 1 or Formula 2 are particularly useful in combination with spectral sensitizing dyes. Addition is preferably done as an aqueous solution although any solvent can be used provided the emulsion properties are not effected in a deleterious manner. The supersensitizer can be added in an amount of 0.01 to 10 g. per mole of silver. Preferable is an amount of 0.03 to 5.0 g per mole of silver and most preferable is an amount of 1.0 to 5.0 g per mole of silver. Addition can be anytime during the emulsion preparation procedure with the preferred addition time being after grain growth and prior to the initiation of chemical sensitization.

Compounds of Formula 1 can be ortho, meta or para substituted with ortho substituted preferred. The counterion is not particularly critical provided solubility is acceptable. Preferred counterions are sodium, lithium, potassium and ammonium with sodium most preferred due to commercial availability.

Compounds of Formula 2 are easily prepared from compounds of Formula 1 as known in the art by the simple mixing of compounds of Formula 1 with a polyvinyl alcohol at a pH of 5.8–6.4 in an alcohol-water mixture according substantially to the following reaction:

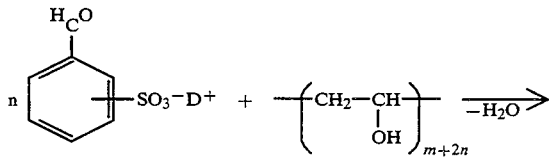

-continued

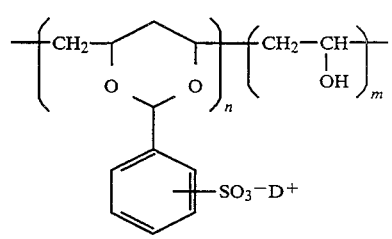

For Formula 2, preferred values of n are 1 to 5. Most preferable is n equal to 1. Preferred values of m are 1 to 10, more preferred is a value of 1 to 5 and most preferred is m equal to 3. The counterion is not particularly critical provided solubility is acceptable. Preferred counterions are sodium, lithium, potassium, and ammonium with sodium most preferred.

Derivitized versions of Formula 1 and Formula 2 are envisioned within the metes and bounds of the teachings herein including substitutions on the aromatic ring, heteroatom ring analogues, substitutions in the polymer chain and the like provided the sensitometric properties of the resulting photographic element are not compromised.

The following sensitizing dyes are exemplary examples of dyes defined by Formula 3 and are not intended to limit the invention in any way.

Inventive SD-1

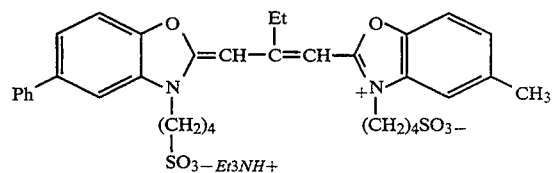

Inventive SD-2

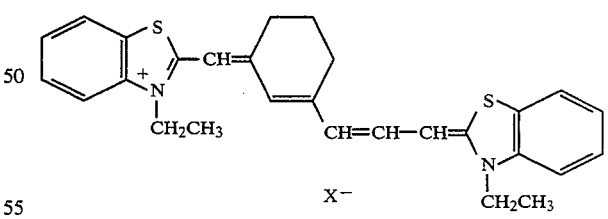

Inventive SD-3

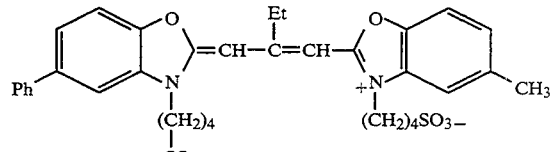

Inventive SD-4

-continued

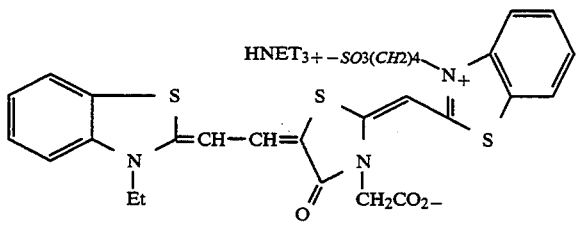

The following sensitizing dyes are exemplary examples of dyes defined by Formula 4 and are not intended to limit the invention in any way.

Inventive SD-5

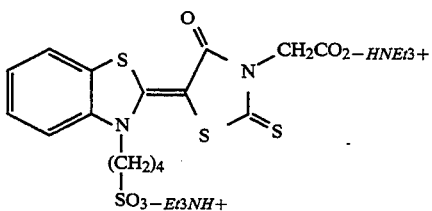

Inventive SD-6

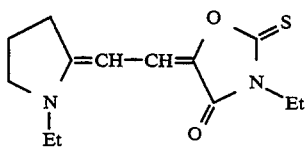

Inventive SD-7

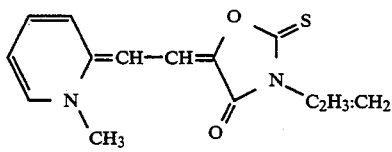

The dyes can be added as a solution, a solid or other means as known in the art. Typically, the dye is added in an amount of 1 mg to 5 g of dye per mole of silver although more or less may be appropriate for some dyes. Dye addition can occur at any time during the emulsion preparation process including during grain growth, prior to chemical sensitization, during chemical sensitization or after chemical sensitization is complete. Most preferred is dye addition after chemical sensitization is complete.

The term "ultrafiltration" is used in accordance with the definition provided in Ultrafiltration Handbook, M. Chenyan, Technomic Publishing Company, Inc., 1986. A specific example of the use of ultrafiltration in photographic element is provided in Research Disclosure, Volume 102, October 1972, Item 10208. Ultrafiltration, also referred to as diafiltration, is widely known in the art as a purification process with particular applicability during grain preparation and purification. In general, membranes are employed which allow passage of undesirable materials and exclude passage of desirable materials such as the silver halide grain.

The ultrafiltration process comprises washing and/or concentrating silver halide emulsions to remove extraneous soluble salts. This is accomplished by passing the peptized silver halide precipitate, or emulsion, through a pressurized ultrafiltration module such that the extraneous salts pass through a semipermeable membrane and a retentate is obtained comprising the silver halide emulsion and a peptizer. The selective separation is affected by hydraulically pressuring a solution against a synthetic semi-permeable membrane which is constructed so as to selectively pass all molecules below a particular size and retain the larger molecules.

The precipitated silver halide in a peptizer solvent and extraneous salts are supplied to the reservoir by well known means. The solution is then pumped through a process flowmeter into the ultrafiltration module. The extraneous salts are extracted as the permeate whereas the retentate is passed back into the reservoir in a recycle operating mode. In the alternative, a number of ultrafiltration modules may be connected in series such that the retentate from the preceding module is fed into the input line of the succeeding module. Prior to the successive passing of the solution through the modules the solution can be rediluted with solvent for washing purposes or in the alternative the solution need not be rediluted for purposes of concentration.

The molecular weight cut off is typically from about 500 to about 300,000. However, molecular weight cut-off can be readily varied outside the preferred range. It is readily understood that the molecular weight cut off should be generally not greater than the molecular weight of the peptizer.

The input pressure maintained over the membrane can vary over a wide range as detailed in Research Disclosure, Volume 102, October 1972, Item 10208. Typically the input pressure is about 100 psi and the outlet pressure is up to about 10 psi. The transmembrane pressure can be from about 40 psi to about 60 psi. These pressures can vary above and below these figures and are limited only by such factors as the capabilities of the pumping equipment, the viscosity and concentration of the retentate, the degree of purity desired for the retentate, the desired flow rate and other factors which would be well known in the art.

Silver halide crystals freshly formed in the presence of a peptizer can be washed or purified by passing a solution of the freshly precipitated silver halide through an ultrafiltration module. The washing or passage through an ultrafiltration module is continued until the silver halide is substantially free of soluble extraneous ions such as, for example, nitrate ions or soluble halide ions. Typically the silver halide solution is passed through an ultrafiltration module a plurality of times, the number of times being dependant on such factors as the soluble salt concentrations obtained during formation, the melt weight, the silver halide to peptizer ratio, etc. It is generally the practice to wash the silver halide emulsions until the pAg has been lowered to about 8. It has generally been found that the soluble salt content decreases in accordance with a mass balance from one cycle to the next.

Any of the conventional halides may be used in this invention. Any grain morphology is suitable for demonstration of these teachings including, but not limited to, grains which are formed by splash techniques and those formed by techniques involving spray techniques. Tabular grains as taught by Nottorf, U.S. Pat. No. 4,722,886 or Ellis, U.S. Pat. No. 4,801,522 are exemplary. Cubic grains are most preferred.

The grains are preferably dispersed in a binder (e.g. gelatin or other well-known binders such as polyvinyl alcohol, phthalated gelatins, etc.). In place of gelatin other natural or synthetic water-permeable organic colloid binding agents known in the art can be used as a total or partial replacement thereof. It is common to use binder adjuvants useful for increasing covering power such as dextran or the modified, hydrolysed gelatins of Rakoczy, U.S. Pat. No. 3,778,278.

It is most preferable to chemically sensitize the grain with salts that are well known in the art. The most common sensitizers are salts of gold or sulfur. Sulfur sensitizers include those which contain labile sulfur, e.g. allyl isothiocyanate, allyl diethyl thiourea, phenyl isothiocyanate and sodium thiosulfate for example. The polyoxyalkylene ethers in Blake et al., U.S. Pat. No. 2,400,532, and the polyglycols disclosed in Blake et al., U.S. Pat. No. 2,423,549. Other non-optical sensitizers such as amines as taught by Staud et al., U.S. Pat. No. 1,925,508 and Chambers et al., U.S. Pat. No. 3,026,203, and metal salts as taught by Baldsiefen, U.S. Pat. No. 2,540,086 may also be used.

The emulsions can contain known antifoggants, e.g. 6-nitrobenzimidazole, benzotriazole, triazaindenes, etc., as well as the usual hardeners, i.e., chrome alum, formaldehyde, dimethylol urea, mucochloric acid, etc. Other emulsion adjuvants that may be added comprise matting agents, plasticizers, toners, optical brightening agents, surfactants, image color modifiers, print-through reduction dyes, and covering power adjuvants among others.

The film support for the emulsion layers may be any suitable transparent plastic. For example, the cellulosic supports, e.g. cellulose acetate, cellulose triacetate, cellulose mixed esters, etc. may be used. Polymerized vinyl compounds, e.g., copolymerized vinyl acetate and vinyl chloride, polystyrene, and polymerized acrylates may also be mentioned. When polyethylene terephthalate is manufactured for use as a photographic support, it is preferable to use a mixed polymer subbing composition such as that taught by Rawlins, U.S. Pat. No. 3,567,452, Miller, U.S. Pat. Nos. 4,916,011 and 4,701,403, Cho, U.S. Pat. Nos. 4,891,308 and 4,585,730 and Schadt, U.S. Pat. No. 4,225,665.

The emulsions may be coated on the supports mentioned above as a single layer or multi-layer element. For medical x-ray applications, for example, layers may be coated on on both sides of the support which conventionally contains a dye to impart a blue tint thereto. Contiguous to the emulsion layers it is conventional, and preferable, to apply a thin stratum of hardened gelatin supra to said emulsion to provide protection thereto.

The emulsions of this invention can be used in any of the conventional photographic systems (e.g. negative or positive-working systems). Thus, they can contain any of the adjuvants related to the particular system employed. For example, the emulsions when employed as direct positive may be chemically fogged using metals such as rhodium or iridium and the like, or with other chemical fogging agents such as boranes, as well-known to those skilled in the art.

The following examples illustrate some of the advantages of the invention and are not intended to limit the invention in any way.

EXAMPLE 1

A cubic grain with 0.215 μm edges was prepared as known in the art and separated into two aliquots. One aliquot was coagulated and washed (CW) as known in the art and another was ultrafiltered (UF) as known in the art. After chemical sensitization 25 mg of sensitizing dye SD-6 per mole of silver and 131 mg of sensitizing dye SD-7 per mole of silver were added. Supersensitizers SA-1 and SA-2 were added in the amounts shown in Table 1.

SA-1

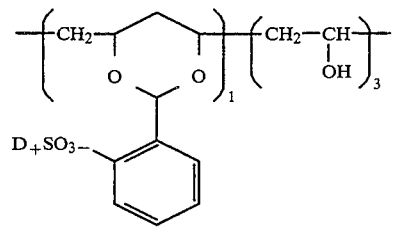

SA-2

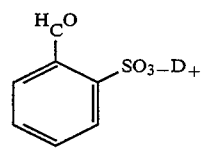

The resulting emulsion was coated, as known in the art, on a subbed polyethylene terephthalate support. Duplicate samples of the film were exposed to green light with a EG&G Xenon Mark VII flash sensitometer with appropriate filters as known in the art. The exposed film was chemically processed and analyzed as known in the art. The relative results were averaged and reported in Table 1 wherein speed is relative to Sample 1.

TABLE 1

| Sample | Grain | Additive | Amount | Speed |
| --- | --- | --- | --- | --- |
| 1 Comp. | CW | SA-1 | 5.56 | 100 |
| 2 Comp. | UF | — | — | 51 |
| 3 Inven. | UF | SA-2 | 2.28 | 135 |
| 4 Inven. | UF | SA-1 | 3.89 | 161 |
| 5 Inven. | UF | SA-2 | 1.14 | 152 |
| 6 Inven. | UF | SA-1 | 1.95 | 127 |

The amounts of additive are listed as grams of additive per mole of silver. The combination of ultrafiltration and the supersensitizer provided a dye sensitized emulsion with a much improved speed over comparable examples.

EXAMPLE 2

A 0.013 $\mu^3$ cubic grain comprising 70% bromide and 30% chloride was prepared as known in the art and separated into two aliquots. One aliquot was coagulated and washed as known in the art and the other aliquot was ultrafiltered as known in the art. The grains were chemically sensitized as known in the art followed by addition of supersensitizing agents as listed in Table 2. The emulsion was spectral sensitization with 16.7 mg of sensitizing dye SD-2 per mole of silver and coated as known in the art. The resulting films were exposed to infrared light with an EG&G sensitometer as described and chemically processed. The results are contained in Table 2. Speed is reported relative to Sample 7, MG is mid-gradiant and DM is maximum density obtained. Amounts of additive are listed as grams per mole of silver.

TABLE 2

| Sample | Grain | Additive | Amount | Speed | MG | DM |
|---|---|---|---|---|---|---|
| 7 Comp. | CW | SA-1 | 4.7 | 100 | 3.75 | 4.07 |
| 8 Comp. | UF | — | — | 66 | 4.43 | 4.41 |
| 9 Inv. | UF | SA-1 | 0.47 | 102 | 4.27 | 4.58 |
| 10 Inv. | UF | SA-1 | 1.02 | 97 | 4.42 | 4.40 |
| 11 Inv. | UF | SA-1 | 1.72 | 119 | 4.55 | 4.59 |

The combination of ultrafiltration, sensitizing dye and the supersensitization additive provides and emulsion with an increased speed and improved mid-gradiant and maximum density.

EXAMPLE 3

The ultrafiltered grains from Example 2 were treated the same as in Example 2 with the following exceptions. The spectral sensitizing dye used was SD-3 and the exposure was with green light using an EG&G spectrometer as described above. The supersensitizing agent SA-1 was used in the amounts listed. The amounts of spectral sensitizing dye are listed as grams of dye per mole of silver. The amount of supersensitizing agent added is listed as grams per mole of silver. The speed is reported relative to Sample 12.

TABLE 3

| Sample | Dye Amount | SA Amount | Speed |
|---|---|---|---|
| 12 Comp. | 1.7 | 0 | 100 |
| 13 Inv. | 1.7 | 1.67 | 111 |
| 14 Comp. | 2.8 | 0 | 143 |
| 15 Inv. | 2.8 | 1.67 | 146 |
| 16 Comp. | 5.6 | 0 | 140 |
| 17 Inv. | 5.6 | 1.67 | 162 |

Example 3 illustrates that the efficiency of the dye is increased when the supersensitizing agent is used in combination with an ultrafiltered grain. With increased dye efficiency a desired speed can be reached with lower amounts of dye. This is most advantageous in the art due to lower material cost and a decrease in the amount of residual dye which is present in the film element after processing.

EXAMPLE 4

A sample was prepared identical to that of Example 2 except for the use of SD-1 sensitizing dye. The results are included in Table 4. The dye amounts are listed as grams of dye per mole of silver and the amounts of SA-1 are listed as grams per mole of silver. Speed is relative to Sample 18.

TABLE 4

| Sample | Dye Amount | SA Amount | Speed |
|---|---|---|---|
| 18 Comp. | 1.7 | 0 | 100 |
| 19 Inv. | 1.7 | 1.67 | 134 |
| 20 Comp. | 2.8 | 0 | 94 |
| 21 Inv. | 2.8 | 1.67 | 128 |

The supersensitizing agent increases the efficiency of the dye as indicated by the increased speed of the emulsion.

EXAMPLE 5

The ultrafiltered grains from Example 2 were treated the same as in Example 2 with the following exceptions. The spectral sensitizing dye was SD-5 and the exposure was with blue light using an EG&G spectrometer as described above. The supersensitizing agent SA-1 was used in the amounts listed in Table 5 which are reported as grams per mole of silver and the amount of supersensitizing dye is reported as mg of dye per mole of silver. Speed is reported relative to Sample 22.

TABLE 5

| Sample | Dye Amount | SA Amount | Speed |
|---|---|---|---|
| 22 Comp. | 66.7 | 0 | 100 |
| 23 Inv. | 66.7 | 1.67 | 110 |
| 24 Comp. | 133.3 | 0 | 140 |
| 25 Inv. | 133.3 | 1.67 | 180 |
| 26 Comp. | 266.7 | 0 | 180 |
| 27 Inv. | 266.7 | 1.67 | 230 |

The addition of the supersensitizer agent increases the efficiency of the dye such that the dye level could be decreased. This is particularly advantageous with dyes which are difficult to remove during processing and which create staining problems due to residual dye. The reduction of the amount of dye used decreases the likelihood of dye retention. Comparing, for example, Samples 25 and 26 the same speed was obtained with half of the dye level when the inventive supersensitizer was used.

EXAMPLE 6

The ultrafiltered grains from Example 2 were treated the same as in Example 2 with the following exceptions. The spectral sensitizing dye was SD-4 and the exposure was with red light using an EG&G spectrometer as described above. The supersensitizing agent SA-1 was used in the amounts listed in Table 6. The dye amounts are listed as mg of dye per mole of silver and the SA-1 amounts are listed as grams per mole of silver. Speed is reported relative to Sample 28.

TABLE 6

| Sample | Dye Amount | SA Amount | Speed |
|---|---|---|---|
| 28 Comp. | 6 | 0 | 100 |
| 29 Inv. | 6 | 1.67 | 120 |
| 30 Comp. | 12 | 0 | 187 |
| 31 Inv. | 12 | 1.67 | 233 |
| 32 Comp. | 24 | 0 | 280 |
| 33 Inv. | 24 | 1.67 | 333 |
| 34 Comp. | 48 | 0 | 260 |
| 35 Inv. | 48 | 1.67 | 300 |

Improved dye efficiency is observed in each case since the speed in increased at a given dye level when the supersensitizer is added.

We claim as our invention:

1. A process for the preparation of a photosensitive silver halide emulsion comprising the steps of:
   a) reacting $Ag^+NO_3^-$ with $G^+X^-$ to form $Ag^+X^-$ and $G^+NO_3^-$; $G^+$ is $Na^+$, $K^+$, $NH_4^+$ or a combination thereof; $X^-$ is $Cl^-$, $Br^-$, $I^-$ or a combination thereof;
   b) decreasing the concentration of $G^+NO_3^-$ by ultrafiltration;
   c) adding at least one compound selected from the group consisting of:

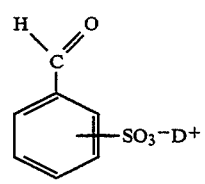

and

-continued

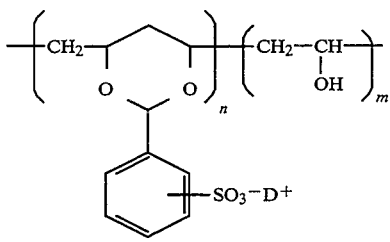

wherein D+ is Na+, K+, Li+, NH4+; n/m is 0.1 to 5.0;

d) adding at least one spectral sensitizer capable of increasing the sensitivity to actinic radiation.

2. The process recited in claim 1 wherein said compound is added in an amount of 0.01 to 10 grams per mole of silver.

3. The process recited in claim 2 wherein said compound is added in an amount of 0.03 to 5.0 grams per mole of silver.

4. The process recited in claim 3 wherein said compound is added in an amount of 1.0 to 5 grams per mole of silver.

5. The process recited in claim 1 wherein said spectral sensitizer is chosen from the set consisting of:

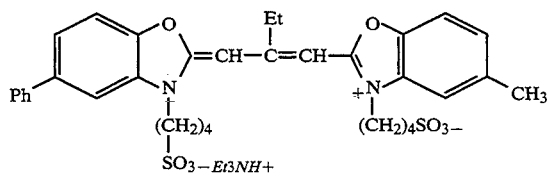

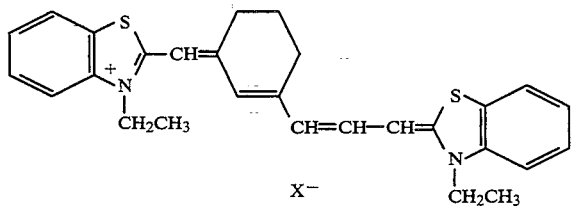

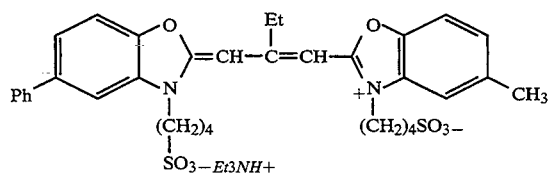

and

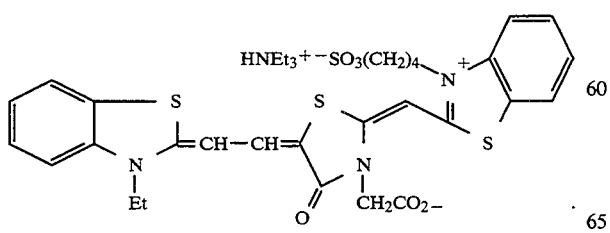

6. The process recited in claim 1 wherein said spectral sensitizer is

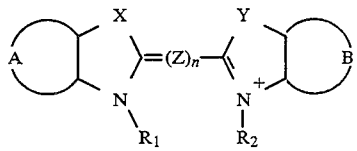

X,Y is oxygen or sulfur;
n is an integer chosen from the set consisting of 1, 3, 5 and 7;
A, B is an aromatic ring;
Z represents a methine;
$R_1$ is an alkyl group;
$R_2$ is an alkyl group or a substituted alkyl group.

7. The process recited in claim 1 wherein said spectral sensitizer is

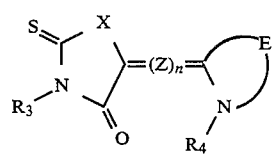

X is oxygen or sulfur;
n is an integer chosen from the set consisting of 0, 2, 4 and 6;
E is an aromatic ring;
Z represents a methine;
$R_3$ is an alkyl group;
$R_4$ is an alkyl group or a substituted alkyl group.

8. The process recited in claim 1 wherein the spectral sensitizer is chosen from the set consisting of:

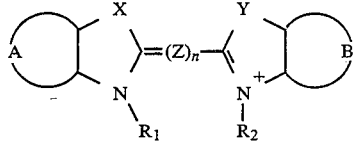

9. A process for the preparation of a photosensitive silver halide emulsion comprising the steps of:

a) reacting Ag+NO3− with G+X− to form Ag+X− and G+NO3− wherein G+ is Na+, K+, NH4+ or a combination thereof; X− is Cl−, Br−, I− or a combination thereof;

b) decreasing the concentration of G+NO3− by ultrafiltration;

c) adding a compound defined by

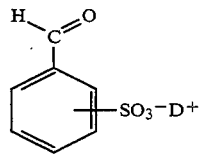

wherein D+ is Na+, K+, Li+ or NH4+;

d) adding at least one spectral sensitizer capable of increasing sensitivity to actinic radiation.

10. The process recited in claim 9 wherein said compound is added in an amount of 0.01 to 10 grams per mole of silver.

11. The process recited in claim 10 wherein said compound is added in an amount of 0.03 to 5.0 grams per mole of silver.

12. The process recited in claim 11 wherein said compound is added in an amount of 1.0 to 5 grams per mole of silver.

13. The process recited in claim 9 wherein said spectral sensitizer is

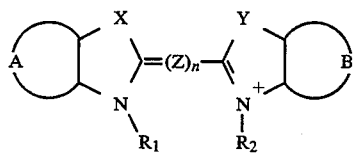

X,Y is oxygen or sulfur;
n is an integer chosen from the set consisting of 1, 3, 5 and 7;
A, B is an aromatic ring;
Z represents a methine;
$R^1$ is an alkyl group;
$R^2$ is an alkyl group.

14. The process recited in claim 9 wherein said spectral sensitizer is chosen from the set consisting of:

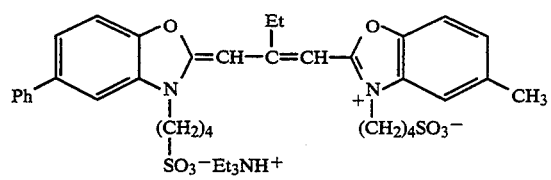

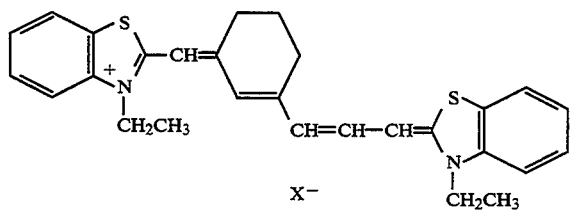

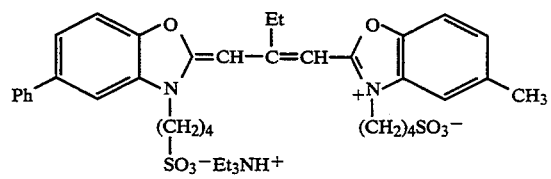

and

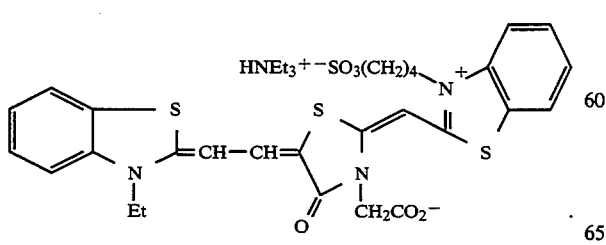

15. The process recited in claim 9 wherein said spectral sensitizer is

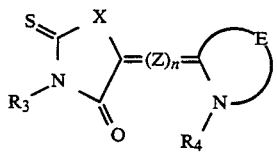

X is oxygen or sulfur;
n is an integer chosen from the set consisting of 0, 2, 4 and 6;
E is an aromatic ring;
Z represents a methine;
$R_3$ is an alkyl group or a substituted alkyl group;
$R_4$ is an alkyl group or a substituted alkyl group.

16. The process recited in claim 9 wherein the spectral sensitizer is chosen from the set consisting of:

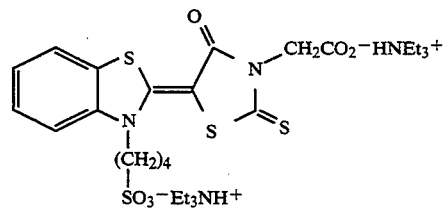

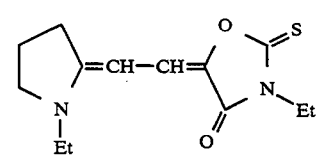

and

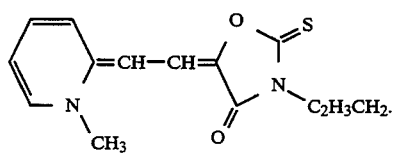

17. A process for the preparation of a photosensitive silver halide emulsion comprising the steps of:
a) reacting $Ag^+NO_3^-$ with $G^+X^-$ to form $Ag^+X^-$ and $G^+NO_3^-$; $G^+$ is $Na^+$, $K^+$, $NH_4^+$ or a combination thereof; $X^-$ is $Cl^-$, $Br^-$, $I^-$ or a combination thereof;
b) decreasing the concentration of $G^+NO_3^-$ by ultrafiltration;
c) adding at least one compound selected from the group consisting of:

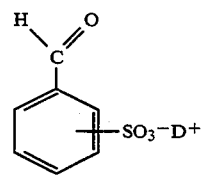

and

-continued

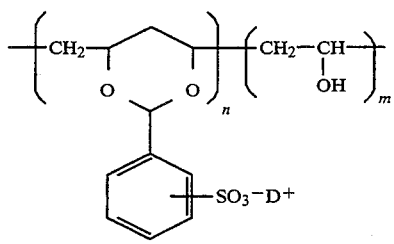

wherein $D^+$ is $Na^+$, $K^+$, $Li^+$, $NH_4^+$; n/m is 0.1 to 5.0;
d) adding at least one spectral sensitizer chosen from the set consisting of:

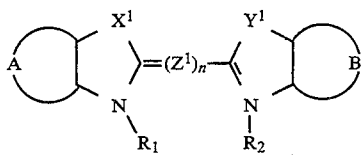  i)

$X^1$, $Y^1$ is oxygen or sulfur;
n is an integer of 1, 3, 5 or 7;
A, B is an aromatic ring;
$Z^1$ is selected from a group consisting of methine, oxazole and thiazole provided that no more than one said $Z^1$ is oxazole or thiazole;
$R^1$ is an alkyl group;
$R^2$ is an alkyl group; and

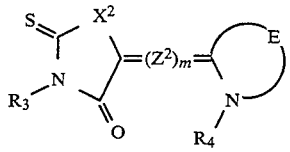  ii)

$X^2$ is oxygen or sulfur;
m is an integer from 0, 2, 4 or 6;
E is an aromatic ring;
$Z^2$ is selected from a group consisting of methine, oxazole and thiazole provided that no more than one said $Z^2$ is oxazole or thiazole;
$R_3$ is an alkyl group or a substituted alkyl group;
$R_4$ is an alkyl group or a substituted alkyl group.

* * * * *